(12) United States Patent
Neuberger

(10) Patent No.: US 6,951,630 B2
(45) Date of Patent: Oct. 4, 2005

(54) METHOD AND SUBSTANCE FOR OBTAINING SURFACES WITH ANTIMICROBIAL PROPERTIES

(75) Inventor: Wolfgang Neuberger, F.T. Labuan (MY)

(73) Assignee: CeramOptec Industries, Inc., East Longmeadow, MA (US)

( * ) Notice: Subject to any disclaimer, the term of this patent is extended or adjusted under 35 U.S.C. 154(b) by 162 days.

(21) Appl. No.: 09/931,265

(22) Filed: Aug. 16, 2001

(65) Prior Publication Data

US 2003/0035750 A1 Feb. 20, 2003

(51) Int. Cl.[7] ............................................... A61L 2/00
(52) U.S. Cl. ........................... 422/22; 422/24; 422/28
(58) Field of Search .............................. 422/22, 24, 28

(56) References Cited

U.S. PATENT DOCUMENTS

| | | | |
|---|---|---|---|
| 4,318,883 A | * | 3/1982 | Polony et al. ............. 422/22 |
| 4,532,269 A | | 7/1985 | Gitlitz et al. |
| 5,534,346 A | | 7/1996 | Robinson |
| 5,967,714 A | | 10/1999 | Ottersbach et al. |
| 6,080,490 A | | 6/2000 | Burrell et al. |
| 6,107,326 A | * | 8/2000 | Jori ............................ 514/410 |
| 6,214,901 B1 | | 4/2001 | Chudzik et al. |

FOREIGN PATENT DOCUMENTS

| WO | WO 93/00815 | * | 1/1993 |
|---|---|---|---|
| WO | WO 01/34211 A2 | * | 5/2001 |

* cited by examiner

Primary Examiner—Krisanne Jastrzab
(74) Attorney, Agent, or Firm—BJ Associates; Bolesh J. Skutnik

(57) ABSTRACT

The present invention involves the use of photosensitizers to provide antibacterial surfaces on consumer and industrial items. This approach avoids the used of chemicals and solutions that may be toxic. The inventions also avoids the use of chemical compositions that might form degradation products which may be unacceptable to healthy persons or irritating to persons who may have allergies or are otherwise sensitized. According to the invention, photosensitizers with specific properties and specific design features are selected to make practical use of photosensitizers in the consumer and industrial market place. It is important to select a photosensitizer with an activation spectrum that is matched to the environmental conditions under which the surface to be protected is required to exhibit its antimicrobial properties. This means that the illumination energy and intensity levels expected need to yield enough singlet oxygen to destroy the targeted microbes. It is also possible to select photosensitizers that are activated only by wavelengths prominently present in certain illumination lamps, such as those lamps commonly present in a laboratories, medical offices, pharmacies and food service areas, thereby making the surfaces antimicrobial only on demand when the illumination lamps are turned on.

11 Claims, 1 Drawing Sheet

METHOD AND SUBSTANCE FOR OBTAINING SURFACES WITH ANTIMICROBIAL PROPERTIES

BACKGROUND OF THE INVENTION

1. Field of the Invention

The present invention relates to products and methods to provide common surfaces with antimicrobial properties to fight bacteria, viruses and fungi.

2. Invention Disclosure Statement

Surfaces of many consumer goods and industrial items are regularly populated by bacteria, viruses and fungi, which can produce health hazards. Cleaning and disinfecting these common surfaces is an everyday hygienic process. Cleaning and disinfecting do not always yield satisfactory results, since many microbes have increasingly become resistant to many of the agents currently being used. Chemical compositions used to disinfect surfaces often have a broad non-specific action and may be health risks to people with allergies or chemical sensitivities.

U.S. Pat. No. 4,532,269 describes a terpolymer that is used as an antimicrobial paint for ships. The coating slowly erodes to produce a highly toxic compound that keeps the paint antimicrobially active. Coatings of this type will lose their action when the active ingredient in the paint eventually migrates to an ineffective level. The toxic compounds created by this invention make it impractical for use in consumer goods or common industrial items.

U.S. Pat. No. 5,534,346 describes an attachable thin film prophylactic barrier used to prevent the spread of infectious disease during medical procedures. The invention is visually transparent or translucent plastic sheet with a pressure sensitive adhesive back. The described invention is a physical barrier and does not have any antimicrobial properties.

U.S. Pat. No. 5,967,714 describes a process for the preparation of antimicrobial polymer surfaces wherein tert-butylaminoethyl methacrylate is graft copolymerized with an aliphatically unsaturated monomer on a polymer substrate. The substrates surface is activated by methods such as UV radiation before the graft polymerization takes place. The described invention is limited to polymer substrates, and antimicrobial protection is only provided at the time the product is manufactured. The invention does not describe how to provide antimicrobial properties to a previously manufactured item.

U.S. Pat. No. 6,214,901 describes a composition for coating a medical device with bioactive agent in a manner that permits the coating to release the bioactive agent over time when implanted in vivo. The described coating composition is particularly adapted for use with devices that undergo significant flexion or expansion in their use. Covering consumer items with the described bioactive agent coatings is not practical since it can interfere with the appearance and utility of the items to be protected.

U.S. Pat. No. 6,080,490 describes an actively sterile surface for a substrate in a biologically dynamic environment. The described invention consists of an antimicrobial element in combination with an electrochemically nobler element that forms multitudinous galvanic cells with biological fluids to release the antimicrobial elements at the target site. Since most commercial and industrial items do not contact biological fluids, use of the described invention to protect such surfaces is not feasible.

U.S. Pat. No. 5,534,346 describes an attachable thin film prophylactic barrier used to prevent the spread of infectious disease during medical procedures. The invention is visually transparent or translucent plastic sheet with a pressure sensitive adhesive back. The described invention is a physical barrier and does not have any antimicrobial properties.

The inventor has previously described (in co-pending U.S application Ser. No. 09/345282 filed on Jun. 30, 1999) medical catheters and implants whose surfaces are covered by photosensitizers or contain photosensitizers. An embodiment of the invention has a photosensitizing compound affixed to or near the device surface with means to periodically activate the compound by suitable illumination. Bacterial growth and adherence to medical devices is overcome for extended periods of time by using the invention. It is impractical to cover consumer items in a similar manner as bleaching will occur over time due to exposure of the surfaces to ambient light. The use of laser as the activation radiation may also be impractical.

It would be useful to have a method to impart antimicrobial properties to product surfaces after they are manufactured, where the microbial action is renewable, and where the microbial agent does not permit the development of resistance by the microbes.

OBJECTS AND BRIEF SUMMARY OF THE INVENTION

An object of the present is to provide a product, which imparts antimicrobial protection to surfaces on consumer and industrial items, which are difficult or impossible for microbes to build immunity to.

Another object of the present invention is to provide a method to reduce the possibility of microbe adherence on commercial surfaces or consumer products by continuously activating a protective coating, which is capable of inhibiting microbial growth on the surface or product.

Yet another object of the present invention is to provide a method to deter microbial growth on surfaces and products by periodically activating a protective coating, which is capable of inhibiting microbial growth on the surface or product.

A further object of the present invention is to provide a plurality of antimicrobial protective layers on an object, which can be peeled away individually to provide new antibacterial surfaces as needed.

Briefly stated, the present invention involves the use of photosensitizers to provide antibacterial surfaces on consumer and industrial items. This approach avoids the use of chemicals and solutions that may be toxic. The invention also avoids the use of chemical compositions that might form degradation products that may be unacceptable to healthy persons or irritating to persons who may have allergies or are otherwise sensitized. According to the invention, photosensitizers with specific properties and specific design features are selected to make practical use of photosensitizers in the consumer and industrial market place. It is important to select a photosensitizer with an activation spectrum that is matched to the environmental conditions under which the surface to be protected is required to exhibit its antimicrobial properties. This means that the illumination energy and intensity levels expected need to yield enough singlet oxygen to destroy the targeted microbes. It is also possible to select photosensitizers that are activated only by wavelengths prominently present in certain illumination lamps, such as those lamps commonly present in a laboratories, medical offices, pharmacies and food service areas, thereby making the surfaces antimicrobial only on demand when the illumination lamps are turned on. A useful feature of the current invention is the lack of antimicrobial resistance to the photodynamic process. It is also useful that photosensitizers are known to be effective against bacteria in a dosage of only one percent required to kill cells.

The above, and other objects, features and advantages of the present invention will become apparent from the following description read in conjunction with the accompanying drawings, (in which like reference numbers in different drawings designate the same elements.)

DETAILED DESCRIPTION OF PREFERRED EMBODIMENTS

Figure 1:
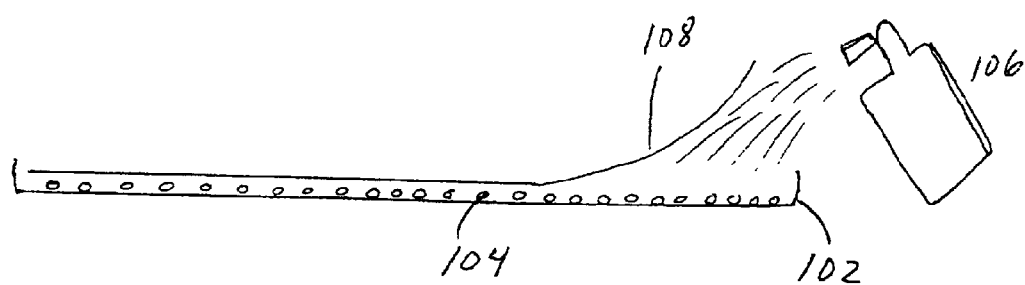
FIG. 1 illustrates a product having a photosensitizer-coated surface with a removable protective layer.

In a preferred embodiment of the present invention, a photosensitizer containing formulation is in a topically applicable form such as a spray or a solution. The antimicrobial formulation will typically consist of a photosensitizer in an aqueous carrier and additional components such as buffers, salts, drying agents, antioxidants, and preservatives.

The photosensitizer containing formulation is maintained in a functional protective environment, such as a spray can or applicator, which protects the photosensitizer containing formulation from activation radiation and oxidation. The phosensitiser formulation is sprayed or applied to a surface or object where antimicrobial properties are desired. The photosensitizer in the formulation is capable of being activated at the environmental conditions under which the surfaces or the products are required to exhibit antimicrobial activity.

In an alternative embodiment, antimicrobial properties are imparted to a surface by applying a photosensitizer containing formulation in a topically available form where the photosensitizer is capable of being activated only at a specific wavelength range. For example, wavelengths prominently present in illumination lamps, such as those lamps commonly present in laboratories, medical offices, pharmacies and food service areas. Such formulations would be activated or reactivated when specific lights were turned on, making the surfaces antimicrobial only on demand. This would minimize the need to reapply the formulation.

In another preferred embodiment of this invention, the photosensitizer formulation is enhanced to protect surfaces where difficult strains of microbes, like certain types bacteria, might be a problem. The formulation components bonds or links the photosensitizer molecules to the surface to be protected. The linking mechanism is designed so that it can be cleaved when exposed to a sufficient concentration of singlet oxygen. The photosensitizer is preferentially modified to have a targeting molecule attached that is designed to target or be attractive to the problem bacteria.

When exposed to short periods of irradiation, enough singlet oxygen is released to cleave the link to the surface, thereby freeing photosensitizer molecules. When the irradiation source is turned off and the singlet oxygen concentration falls below that capable of damaging the bacteria, bacteria will have an opportunity to appear. The targeting molecule will cause the photosensitizer to be brought into close proximity of the bacteria, and preferably absorbed into the bacteria. When the surface to be protected is subsequently illuminated, the photosensitizer will again produce singlet oxygen on or in the targeted bacteria and thereby exhibit a localized and enhanced antimicrobial effect. If a timer controls the illumination source, then this bait and kill enhanced mode of protection can be effective at any time of the day.

The present invention is further illustrated by the following examples, but is not limited thereby.

EXAMPLE 1

In a preferred embodiment, the present invention utilizes a protective layer on the photosensitizer treated surface, such as a protective foil. This serves to shield the photosensitizer containing formulation on the surface below the protective layer from oxygen and from the harmful part of the spectrum until the protective layer is removed or stripped off. An example application may be a dental or surgical tray (See FIG. 1). Tray 102 is coated with photosentiser containing formulation 104 using spray can 106 or some other applicator and then covered with protective layer 108. When tray 102 is ready for use, protective layer 108 is removed and the antimicrobial properties of the exposed photosentiser formulation 104 begin. Protective layer 108 could be made from any material that performs the required function, but metal foil, polymer film and paper sheeting will be the most likely materials.

EXAMPLE 2

Figure 2:
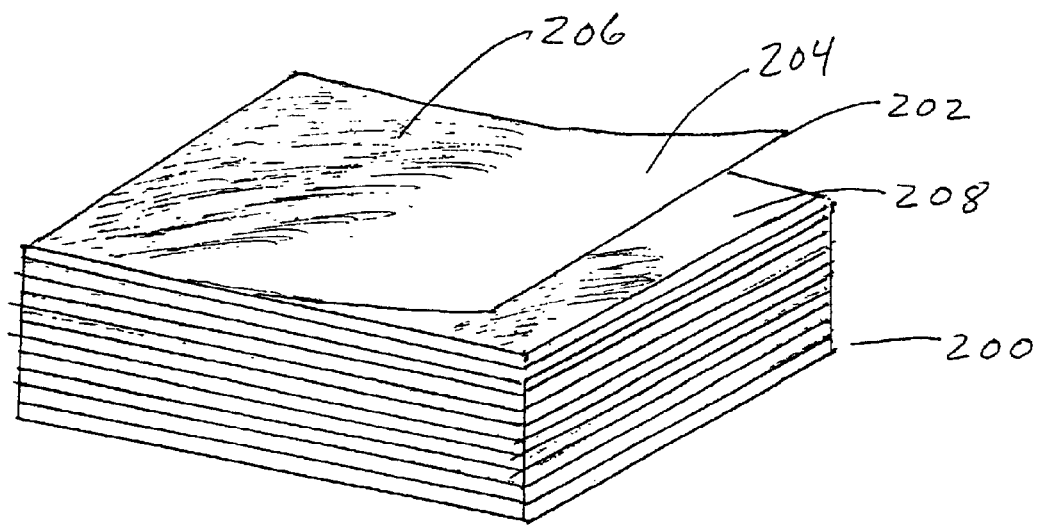
FIG. 2 illustrates a product having a multitude of photosensitizer-coated surfaces each having a removable protective layer.

In another preferred embodiment, a multitude of layers are assembled like pad 200 to form a work surface. (See FIG. 2) Each layer consists of a sheet 202 with each sheet protecting next lower sheet 208. The upper surface 204 of each sheet 202 is coated with photosensitizer formulation. 206. Sheets 202 are opaque to the activation illumination wavelength of the photosensitizer and serve to protect next lower sheet 208. When the antimicrobial activity of photosensitizer formulation 206 on sheet 202 starts to diminish, sheet 202 is stripped off to reveal next lower sheet 208 whose antimicrobial properties are activated when illuminated by the selected light sources. Additional sheets are stripped off as required.

One particular application of this embodiment would be in the food services industry where bacteria and food poisoning are great concerns. By having a multitude of sheets coated with a photosensitizer formulation, a renewable antimicrobial-resistant work surface is readily available. Utensils can be placed on the sheets prior to or between uses. When the sheet has reached its expected effective use, or when the sheet becomes contaminated, the uppermost sheet in the pad can be peeled away, revealing a new sheet coated with the photosensitizer formulation. Since the described invention has no hazardous chemicals associated with it, it is ideal for use in the food service industry. The sheets could be made from any material that that performs the required functions, but metal foil, polymer film and paper sheeting will be the most likely materials.

Having described preferred embodiments of the invention with reference to the accompanying drawings, it is to be understood that the invention is not limited to the precise embodiments, and that various changes and modifications may be effected therein by skilled in the art without departing from the scope or spirit of the invention as defined in the appended claims.

What is claimed is:

1. A method for imparting antimicrobial properties to a surface comprising:
   a) selecting a photosensitizer capable of being activated by an environmental condition, under which said surface is required to exhibit antimicrobial activity;
   b) preparing a photosensitizer containing formulation from said photosensitizer in a topically available form, wherein said photosensitizer is preferentially modified to have a targeting molecule attached;
   c) applying said photosensitizer containing formulation to said surface, wherein said photosensitizer is bonded to said surface and;
   d) exposing said photosensitizer to said environmental condition.

2. The method of claim 1 wherein said environmental condition is ambient light.

3. The method of claim 1 wherein said environmental condition is a specific illumination source, operating at wavelengths above the ultraviolet region of the electromagnetic spectrum.

4. The method of claim 1 wherein said topically available form is as a spray.

5. The method of claim 1 wherein said topically available form is a solution.

6. The method of claim 1 wherein said bond being cleavable by singlet oxygen.

7. The method of claim 1 wherein said targeting molecule is selected to target and be attractive to predetermined microbes.

8. The method of claim 6 wherein said surface bonded with said photosensitizer is exposed to short periods of said environmental condition to release singlet oxygen and cleave said linking mechanism, followed by a period of no exposure to said environmental condition to allow microbes to contact or absorb said photosensitizer, and then long periods of said environmental condition to produce singlet oxygen to destroy said microbes.

9. A product having a surface coated with a photosensitizer containing formulation for imparting antimicrobial properties to a surface, comprising a photosensitizer in a topically available form capable of being activated by environmental conditions, under which said surface is required to exhibit antimicrobial activity, wherein said photosensitizer is preferentially modified to have a targeting molecule attached, said targeting molecule selected to target and be attractive to predetermined microbes, said surface having a removable protective layer that protects said photosensitizer from activation illumination and oxygen, wherein said removable protective layer is selected from the group consisting of metal foil, plastic film and paper sheeting.

10. A product having a multitude of layers, where each of said layers is comprised of a sheet having an upper surface coated with a photosensitizer containing formulation, each of said sheets protecting an upper surface on a next lower sheet, from activation illumination and oxygen.

11. The product of claim 10 wherein said photosensitizer is preferentially modified to have a targeting molecule attached, said targeting molecule selected to target and be attractive to predetermined microbes.

* * * * *